United States Patent [19]
Amyette

[11] Patent Number: 5,931,845
[45] Date of Patent: Aug. 3, 1999

[54] PIERCED BODY PART CLEANING DEVICE

[76] Inventor: Carol R. Amyette, 7134 McCurley Rd., Acworth, Ga. 30102

[21] Appl. No.: 09/027,135

[22] Filed: Feb. 20, 1998

[51] Int. Cl.$^6$ ........................................................ A61F 9/00
[52] U.S. Cl. .......................... 606/162; 606/161; 606/167; 606/131; 606/168; 604/1
[58] Field of Search ..................................... 606/162, 161, 606/131, 167, 168; 604/1; 15/23

[56] References Cited

U.S. PATENT DOCUMENTS

| | | | |
|---|---|---|---|
| 1,417,725 | 5/1922 | Fullenwider | 15/184 |
| 1,573,648 | 2/1926 | Sheely | 604/1 |
| 4,041,946 | 8/1977 | Barton . | |
| 4,227,537 | 10/1980 | Suciu et al. . | |
| 4,259,850 | 4/1981 | Lalieu . | |
| 4,353,370 | 10/1982 | Evans . | |
| 4,497,402 | 2/1985 | Karos . | |
| 4,600,008 | 7/1986 | Schmidt . | |
| 5,183,461 | 2/1993 | Hobbs . | |
| 5,209,757 | 5/1993 | Krug et al. . | |
| 5,370,651 | 12/1994 | Summers | 606/168 |
| 5,496,338 | 3/1996 | Miyagi et al. . | |

*Primary Examiner*—Michael Buiz
*Assistant Examiner*—(Jackie) Tan-Uyen Ho
*Attorney, Agent, or Firm*—Kenneth L. Tolar

[57] ABSTRACT

A motorized pierced body part cleaning device includes a substantially hollow, elongated tubular handle component having an open end and a plurality of cleaning stem gripping members at a distal end. The cleaning stem gripping members are selectively rotated using an electric motor disposed within the tubular handle. Integral with the tubular handle adjacent its open end is a storage reservoir for storing a plurality of cleaning stems in a cleaning or disinfecting solution. The open end may be selectively enclosed using a cap means.

10 Claims, 2 Drawing Sheets

PIERCED BODY PART CLEANING DEVICE

BACKGROUND OF THE INVENTION

The present invention relates to a hand held motor driven device which allows a user to clean, sterilize or minimize infection of a pierced body part such as an earlobe more efficiently and with minimal effort.

DESCRIPTION OF THE PRIOR ART

Various devices for cleaning a pierced earlobe and the like are known in the prior art. However, none of these devices relate to a motor driven cleaning stem in combination with the various other features of the present invention. For example, U.S. Pat. No. 5,183,461 issued to Hobbs discloses a method for cleaning pierced earlobes using a strand of flexible nylon like material having a loop on an end thereof.

U.S. Pat. No. 4,041,946 issued to Barton relates to a medicated member for cleaning pierced ears comprising an elongated flexible member wrapped with a fibrous material.

U.S. Pat. No. 5,496,338 issued to Miyagi et al relates to a motorized tubular brush for treating sinusitis having a pistol grip type housing with an elongated tubular brush component extending from a distal end thereof.

U.S. Pat. No. 5,209,757 issued to Krug et al relates to an illuminated ear cleaning device including a handle with an ear cleaning means, an illuminating means and a magnifying means thereon.

U.S. Pat. No. 4,227,537 issued to Suciu et al relates to an elongated endometrial brush having a slidable protective sleeve for protecting the brush bristles.

The above described methods and devices designed to clean a pierced ear lobe are inadequate for several reasons. Each of the above mentioned cleaning strands must be inserted into the pierced opening and manually oscillated or rotated which is tedious and awkward. Furthermore, cleaning a pierced earlobe by hand is time consuming, inconvenient and laborious. Finally, manually cleaning a pierced earlobe generally is insufficient since the speed and force of the manual oscillation and/or rotation is limited. The present invention also uses a specially designed cleaning stem that has a more efficient and less abrasive cleaning surface.

SUMMARY OF THE INVENTION

The present invention overcomes the disadvantages of the prior art by providing a motorized pierced body part cleaning device comprising an elongated, hollow tubular handle having an open end. Received within the tubular handle is an electric motor. The electric motor may be actuated using a switch means located on the exterior surface of the tubular handle.

Extending from a distal end of the handle are a plurality of gripping members for receiving and selectively engaging the exterior surface of an accompanying cleaning stem. The gripping members are selectively operable between an open and closed position with a switch slidable within a longitudinal slot disposed on the exterior surface of the elongated handle. The gripping members are in communication with the electric motor allowing selective rotation thereof. Integral with the tubular handle and proximal its open end is a storage chamber for receiving and storing a plurality of cleaning stems and a cleansing solution. The open end of the tubular handle and thus the storage chamber is selectively enclosed using a cap. It is therefore an object of the present invention to provide a pierced body part cleaning device having a cleaning stem which may be rotated by an electric motor.

It is another object of the present invention to provide a pierced body part cleaning device having an integral storage reservoir for storing cleaning stems in a cleansing solution.

It is yet another object of the present invention to provide a pierced ear cleaner which is easy to use and inexpensive to manufacture. Other objects, features and advantages of the present invention will become readily apparent from the following detailed description of the preferred embodiment when considered with the attached drawings and the appended claims.

DESCRIPTION OF THE PREFERRED EMBODIMENT

Figure 1:
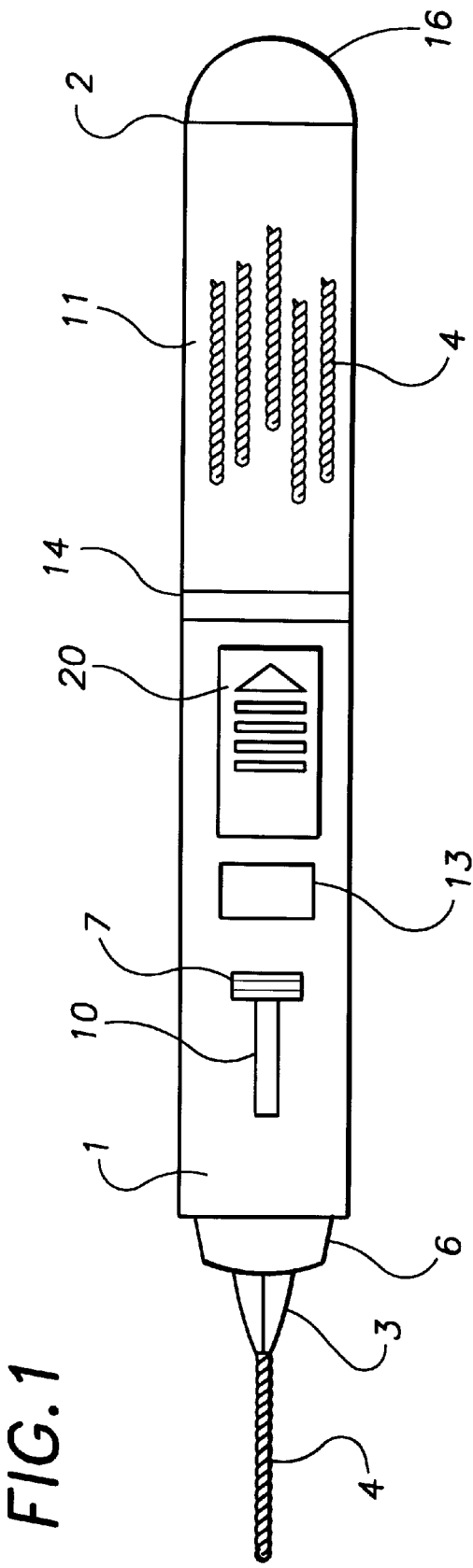
FIG. 1 depicts the inventive device.
Figure 2:
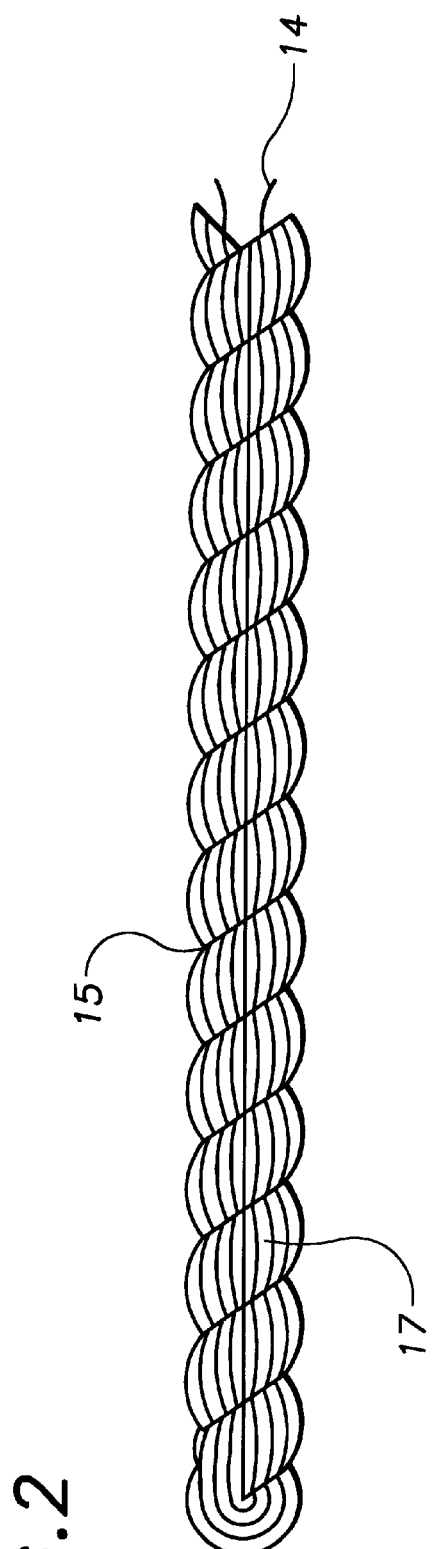
FIG. 2 depicts a cross sectional view of a typical cleaning stem according to the present invention.
Figure 3:
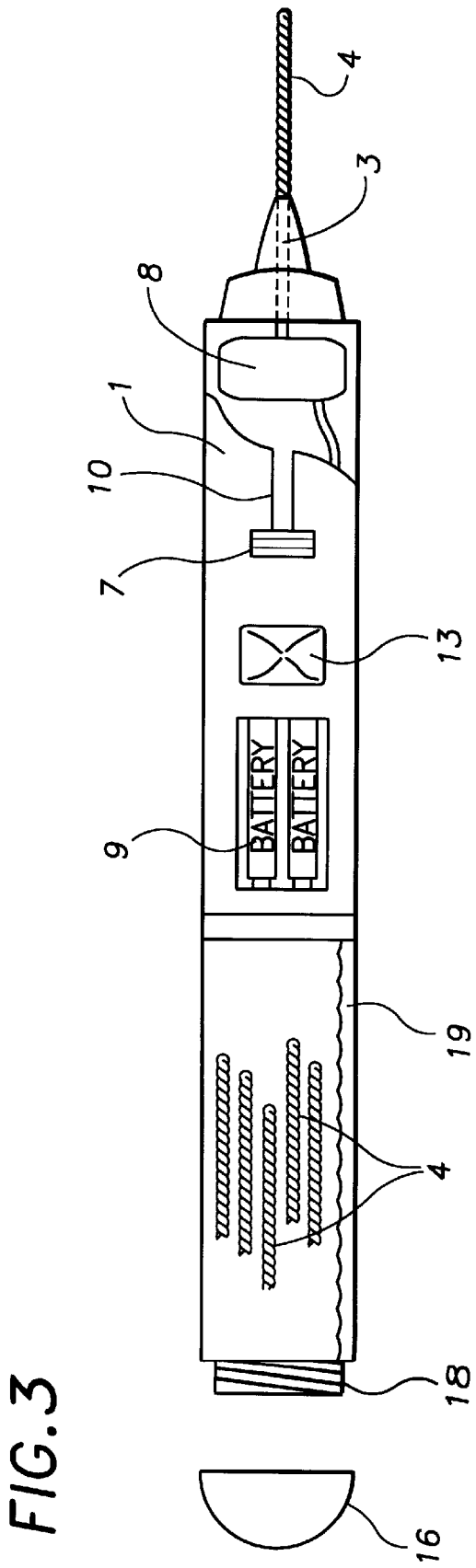
FIG. 3 depicts the inventive device with the electric motor received therein.

Referring now to FIGS. 1 through 3, the present invention relates to a motorized pierced ear cleaning device comprising an elongated hollow tubular handle 1 having an open end 2, an exterior surface and an inner wall. At an end opposite the open end 2 is a leaning stem holder 6 comprising a plurality of gripping members 3 for tightly engaging the exterior surface of a cleaning stem 4. A switch 7 on the exterior surface of the tubular handle is in communication with the gripping members 3 and is slidable within a longitudinal slot 10. Accordingly, the gripping members are operable between a closed position, in which they tightly engage the exterior surface of the cleaning stem 4, and an open position in which they are displaced therefrom, by sliding the switch 7 within the longitudinal slot 10. The slidable switch 7 and cooperating motor driven gripping members 3 are of the type generally known in the prior and are sometimes referred to as a "collett" such as that found on an electric drill for gripping and rotating a drill bit.

Received within the handle is an electric motor 8 in communication with the cleaning stem holder 6 allowing selective rotation thereof. The electric motor 8 is powered by a battery means 9 electrically connected to the motor 8 and received within the tubular handle. The battery is selectively accessible using a removable cover 20. A power switch 13 on the exterior surface of the tubular handle is connected in series with the motor 8 and battery means 9 for selectively actuating the motor 8.

A circular wall 14 is disposed within the tubular handle at a predetermined distance from its open end and is attached to its interior wall. The area between the circular wall 14, the tubular handle interior wall and the open end 2 define an integral storage reservoir 11 for receiving and storing a plurality of cleaning stems 4 in a cleansing or antiseptic solution 19 such as alcohol, hydrogen peroxide and similar products. Preferably, the tubular handle has a threaded portion 18 immediately adjacent its open end for threadedly engaging a threaded cap 16 which encloses and seals the storage reservoir 11. The cap 16, however, may be attached to the open end of the tubular handle using any other suitable attachment means as long as the cap provides a liquid tight seal. The cap 16 may be dome shaped or rounded so that the tubular handle has an aesthetically pleasing exterior surface although other shapes and designs will suffice without departing from the spirit of the invention.

The cleaning stems 4 each comprise an elongated rigid strand 14 of resilient but slightly flexible material having a predetermined length preferably manufactured from either stainless steel or plastic. Preferably, the strand is doubled back onto itself as depicted in FIG. 2. As will be readily apparent to those skilled in the art, other materials may be used without departing from the scope of the present invention. The strand 14 is covered with a strip of fibrous material 15 wrapped in a substantially helical pattern providing a more effective and less abrasive cleaning surface. Preferably, the strip of fibrous material 15 has a plurality of outwardly extending ribs 17 on its exterior surface. The ribs 17 assist in removing debris and dirt particles from the interior of a pierced body part aperture. The shape, size, materials of construction and color of the various components may be varied to suit a particular application.

As indicated above, the present invention relates to a motorized pierced body part cleaning device which more quickly, easily and conveniently cleans a pierced body part aperture. Although there has been shown and described the preferred embodiment of the present invention, modifications may be made thereto which do not exceed the scope of the appended claims. Therefore, the device is to only be limited by the following appended claims.

What is claimed is:

1. A pierced body part cleaning device comprising:

an elongated tubular substantially hollow handle member having, an exterior surface, an open end and a plurality of gripping members at a distal end;

an electric motor received within said tubular handle and in communication with said gripping members for rotating said gripping members; said gripping members being actuatable between a closed position and an open position;

a cleaning stem removably received within said gripping members; said gripping members tightly engaging the exterior surface of the cleaning stein when in the closed position and said gripping members are displaced therefrom when in the open position.

2. A pierced body part cleaner according to claim 1 wherein said gripping members are actuatable between their open and closed positions using a first switch means in communication with said gripping members, said switch means slidable within a longitudinal slot on the exterior surface of said tubular handle.

3. A pierced body part cleaner according to claim 1 further comprising a second switch means on the exterior surface of said tubular handle for selectively activating said electric motor.

4. A pierced body part cleaner according to claim 1 further comprising a storage reservoir integral with the tubular handle adjacent its open end for receiving a plurality of cleaning stems and a cleansing solution, said open end providing; an access opening to said reservoir.

5. A pierced body part cleaner according to claim 4 wherein said storage reservoir is selectively sealable using a cap attached to the handle at its opera end.

6. A pierced body part cleaner according to claim 1 wherein said cleaning stem comprises an elongated strand of rigid but slightly flexible material wrapped around which is a strip of fibrous material.

7. A pierced body part cleaner according to claim 1 wherein said electric motor is powered by a battery means received within said tubular handle.

8. A pierced body part cleaner according to claim 5 further comprising:

a threaded portion on said tubular handle adjacent its open end;

a threaded portion on said cap for threadedly engaging said threaded portion on said handle.

9. A pierced body part cleaner according to claim 6 wherein said fibrous material has a plurality of ribs extending from its exterior surface to more efficiently clean a pierced body part cavity.

10. A pierced body part cleaner according to claim 6 wherein said fibrous material is helically wrapped around said strand.

* * * * *